(12) United States Patent
Kendrick et al.

(10) Patent No.: US 11,911,571 B2
(45) Date of Patent: Feb. 27, 2024

(54) PACKAGING FOR A MEDICAL DEVICE

(71) Applicant: CONVATEC LIMITED, Flintshire (GB)

(72) Inventors: Andrew Kendrick, Cheshire (GB); Oliver Walter Pfleger, Merseyside (GB); Julie Lambrethsen, Cheshire (GB)

(73) Assignee: ConvaTec Limited, Flintshire (GB)

( * ) Notice: Subject to any disclaimer, the term of this patent is extended or adjusted under 35 U.S.C. 154(b) by 303 days.

(21) Appl. No.: 17/238,322

(22) Filed: Apr. 23, 2021

(65) Prior Publication Data

US 2021/0330929 A1    Oct. 28, 2021

Related U.S. Application Data

(63) Continuation of application No. PCT/GB2021/050981, filed on Apr. 23, 2021.

(30) Foreign Application Priority Data

Apr. 24, 2020   (GB) ................................ 2006057

(51) Int. Cl.
*A61M 25/00*   (2006.01)

(52) U.S. Cl.
CPC ..... *A61M 25/002* (2013.01); *A61M 2205/582* (2013.01); *A61M 2205/583* (2013.01); *A61M 2209/06* (2013.01); *A61M 2210/1096* (2013.01)

(58) Field of Classification Search
CPC ........ B65D 33/2533; A61M 2205/582; A61M 25/002; A61M 2205/583; A61M 2209/06; A61M 2210/1096
USPC ........... 383/63, 364, 210, 200–207; 604/265, 604/172; 206/204, 63, 364, 210
See application file for complete search history.

(56) References Cited

U.S. PATENT DOCUMENTS 3,613,879 A * 10/1971 Kemble ............... B65D 75/326
                                                    206/524.8
3,768,725 A    10/1973 Pilaro
(Continued)

FOREIGN PATENT DOCUMENTS

| EP | 3854438 A1 | 7/2021 |
| EP | 3519031 B1 | 9/2021 |

(Continued)

OTHER PUBLICATIONS

International Search Report; European Patent Office; International Application No. PCT/GB2021/050981; dated Oct. 13, 2021; 3 pages.

(Continued)

*Primary Examiner* — Chun Hoi Cheung
(74) *Attorney, Agent, or Firm* — Taft Stettinius & Hollister LLP; Ryan O. White; Derek B. Lavender (57) ABSTRACT

The present invention relates to packaging 10 for housing a medical device 100. The packaging 10 includes first and second sides 12, 14 sealed or otherwise secured around the periphery thereof to define a plurality of edges. An interaction region 24 is provided and defines a first point of contact for a user of the packaging 100. The packaging 10 also includes a tear-away region 28 which may be at least partially separated from the remainder of the packaging to form an open upper end of the packaging 10, in use. The tear-away region 28 includes an interaction point defining a second point of contact for a user of the packaging 10. A sealing arrangement including first and second sealing members 42, 44 provides a user-sealable seal between the first and second sides 12, 14 of the packaging 10.

29 Claims, 3 Drawing Sheets

(56) References Cited

U.S. PATENT DOCUMENTS

| | | | | |
|---|---|---|---|---|
| 4,986,673 A * | 1/1991 | Bell | ............... | B65D 33/16 383/94 |
| 5,174,658 A * | 12/1992 | Cook | ............... | B65D 33/2533 150/900 |
| 5,226,530 A * | 7/1993 | Golden | ............... | A61M 25/002 206/364 |
| 5,253,754 A * | 10/1993 | Soodak | ............... | A01N 1/0268 493/189 |
| 6,244,467 B1 * | 6/2001 | Lewit | ............... | B65D 55/16 222/541.6 |
| 6,702,462 B2 * | 3/2004 | Richardson | ............... | B65D 75/5811 222/541.6 |
| 6,874,938 B2 * | 4/2005 | Price | ............... | B65D 33/2508 383/122 |
| 6,962,439 B2 * | 11/2005 | Taheri | ............... | B65D 33/2566 383/204 |
| 7,770,726 B2 * | 8/2010 | Murray | ............... | A61M 25/0111 604/265 |
| 8,292,076 B2 * | 10/2012 | Dacey | ............... | B65D 75/5855 206/370 |
| 9,649,472 B2 * | 5/2017 | Kearns | ............... | B65D 75/5805 |
| 9,718,593 B2 * | 8/2017 | Gillespie | ............... | B65B 61/18 |
| 10,434,282 B2 * | 10/2019 | Kearns | ............... | B65D 81/22 |
| 10,793,334 B2 * | 10/2020 | Asai | ............... | B65D 75/5805 |
| 11,406,793 B2 | 8/2022 | Murray et al. | | |
| 11,420,015 B2 | 8/2022 | Palmer | | |
| 11,420,016 B2 | 8/2022 | Palmer | | |
| 11,420,017 B2 | 8/2022 | Hilton et al. | | |
| 11,458,283 B2 | 10/2022 | Fletter et al. | | |
| 11,490,983 B2 | 11/2022 | Knapp et al. | | |
| 11,497,886 B2 | 11/2022 | Nielsen et al. | | |
| 11,497,887 B2 | 11/2022 | Heneghan et al. | | |
| 11,534,325 B2 | 12/2022 | Hvid et al. | | |
| 11,534,573 B2 | 12/2022 | Hannon et al. | | |
| 11,603,243 B2 * | 3/2023 | Takigawa | ............... | B65D 75/5805 |
| 2008/0063324 A1 * | 3/2008 | Bernard | ............... | B65D 75/5811 383/200 |
| 2009/0200198 A1 * | 8/2009 | Guelzow | ............... | B65D 81/3261 422/4 |
| 2011/0308981 A1 | 12/2011 | Dacey | | |
| 2012/0168334 A1 | 7/2012 | Wittrock | | |
| 2015/0265801 A1 * | 9/2015 | Rostami | ............... | A61M 25/002 206/438 |
| 2018/0104447 A1 | 4/2018 | Madlung et al. | | |
| 2018/0162619 A1 | 6/2018 | Kocur et al. | | |
| 2019/0105462 A1 | 4/2019 | Schertiger | | |
| 2019/0126004 A1 | 5/2019 | O'Brien et al. | | |
| 2019/0151610 A1 | 5/2019 | Fletter | | |
| 2020/0016380 A1 | 1/2020 | Murray et al. | | |
| 2020/0222659 A1 | 7/2020 | Schertiger et al. | | |
| 2020/0230349 A1 | 7/2020 | McMenamin et al. | | |
| 2021/0170140 A1 | 6/2021 | Owen et al. | | |
| 2021/0187238 A1 | 6/2021 | O'Brien et al. | | |
| 2021/0228836 A1 | 7/2021 | Terry | | |
| 2021/0228837 A1 | 7/2021 | Palmer | | |
| 2021/0244910 A1 | 8/2021 | O'Brien et al. | | |
| 2021/0275727 A1 | 9/2021 | Farrell et al. | | |
| 2021/0290893 A1 | 9/2021 | Palmer | | |
| 2021/0290894 A1 | 9/2021 | Palmer | | |
| 2021/0290895 A1 | 9/2021 | Nielsen et al. | | |
| 2021/0330929 A1 * | 10/2021 | Kendrick | ............... | A61M 25/002 |
| 2021/0330938 A1 | 10/2021 | Kendrick et al. | | |
| 2021/0338979 A1 | 11/2021 | Palmer | | |
| 2021/0346644 A1 | 11/2021 | Kendrick et al. | | |
| 2021/0346645 A1 | 11/2021 | McMenamin et al. | | |
| 2021/0346647 A1 | 11/2021 | Kendrick et al. | | |
| 2021/0346648 A1 | 11/2021 | Kendrick et al. | | |
| 2021/0386965 A1 | 12/2021 | McMenamin et al. | | |
| 2021/0386969 A1 | 12/2021 | O'Flynn | | |
| 2021/0402135 A1 | 12/2021 | McMenamin et al. | | |
| 2022/0001139 A1 | 1/2022 | Eriksson et al. | | |
| 2022/0008626 A1 | 1/2022 | Farrell et al. | | |
| 2022/0023585 A1 | 1/2022 | Schertiger et al. | | |
| 2022/0054295 A1 | 2/2022 | Becker | | |
| 2022/0126057 A1 | 4/2022 | Eriksson et al. | | |
| 2022/0176068 A1 * | 6/2022 | Pfleger | ............... | A61M 25/0017 |
| 2022/0176069 A1 * | 6/2022 | Jenco | ............... | A61M 27/00 |
| 2022/0211973 A1 | 7/2022 | Palmer | | |
| 2022/0226603 A1 | 7/2022 | Murray et al. | | |
| 2022/0226604 A1 | 7/2022 | Murray et al. | | |
| 2022/0226605 A1 | 7/2022 | Murray et al. | | |
| 2022/0241549 A1 | 8/2022 | Murray et al. | | |
| 2022/0241553 A1 | 8/2022 | Farrell et al. | | |
| 2022/0249805 A1 | 8/2022 | Pedersen | | |
| 2022/0296355 A1 | 9/2022 | Goebel | | |
| 2022/0339326 A1 | 10/2022 | Farrell et al. | | |
| 2022/0339399 A1 * | 10/2022 | Jenco | ............... | A61M 25/002 |
| 2022/0347430 A1 | 11/2022 | Pedersen | | |
| 2022/0370760 A1 | 11/2022 | Murray et al. | | |
| 2022/0379075 A1 | 12/2022 | Hilton et al. | | |
| 2022/0387671 A1 | 12/2022 | Sileika et al. | | |
| 2022/0387673 A1 | 12/2022 | Farrell et al. | | |

FOREIGN PATENT DOCUMENTS

| | | |
|---|---|---|
| EP | 2750749 B1 | 10/2021 |
| EP | 3184140 B1 | 10/2021 |
| EP | 3668555 B1 | 10/2021 |
| EP | 3727550 B1 | 10/2021 |
| EP | 3892320 A1 | 10/2021 |
| EP | 3897480 A1 | 10/2021 |
| EP | 3932438 A1 | 1/2022 |
| EP | 3943140 A1 | 1/2022 |
| EP | 3952929 A1 | 2/2022 |
| EP | 3952969 A1 | 2/2022 |
| EP | 3952973 A1 | 2/2022 |
| EP | 3586901 B1 | 3/2022 |
| EP | 3983023 A1 | 4/2022 |
| EP | 3725355 B1 | 5/2022 |
| EP | 3990084 A1 | 5/2022 |
| EP | 3990085 A1 | 5/2022 |
| EP | 3991773 A1 | 5/2022 |
| EP | 3727549 B1 | 6/2022 |
| EP | 4015008 A1 | 6/2022 |
| EP | 2515988 B2 | 7/2022 |
| EP | 2968842 B1 | 7/2022 |
| EP | 4034178 A1 | 8/2022 |
| EP | 4034181 A1 | 8/2022 |
| EP | 3593850 B1 | 9/2022 |
| EP | 4054663 A1 | 9/2022 |
| EP | 2774648 B1 | 10/2022 |
| EP | 3257546 B1 | 10/2022 |
| EP | 4084848 A1 | 11/2022 |
| EP | 4085962 A1 | 11/2022 |
| EP | 2688629 B1 | 12/2022 |
| EP | 3308823 B1 | 12/2022 |
| GB | 2540125 B | 1/2017 |
| WO | 2021154444 A1 | 8/2021 |
| WO | 2021183718 A1 | 9/2021 |
| WO | 2021219188 A1 | 11/2021 |
| WO | 2021221919 A1 | 11/2021 |
| WO | 2021222642 A1 | 11/2021 |
| WO | 2021242745 A1 | 12/2021 |
| WO | 2022002483 A1 | 1/2022 |
| WO | 2022031550 A1 | 2/2022 |
| WO | 2022053841 A1 | 3/2022 |
| WO | 2022090055 A1 | 5/2022 |
| WO | 2022118010 A1 | 6/2022 |
| WO | 2022118011 A1 | 6/2022 |

OTHER PUBLICATIONS

Written Opinion of the International Searching Authority; European Patent Office; International Application No. PCT/GB2021/050981; dated Oct. 13, 2021; 7 pages.

* cited by examiner

PACKAGING FOR A MEDICAL DEVICE

This application is a continuation of International Application No. PCT/GB2021/050981 filed Apr. 23, 2021 and claims the priority of GB Application No. 2006057.0, filed Apr. 24, 2020. The disclosures of which are hereby incorporated herein in their entirety.

TECHNICAL FIELD OF THE INVENTION

The present invention relates to packaging for a medical device. In particular, the present invention relates to packaging for single-use medical devices, including single-use catheters, especially but not exclusively male single-use catheters.

BACKGROUND TO THE INVENTION

Medical devices (e.g. single-use medical devices) are commonly packaged individually. Generally, this may take the form of a plastic or paper housing sealed in some manner to provide a sealed interior housing the medical device. Typical requirements for such packaging include: the packaging being able to be sealed sufficiently to maintain a sterile internal environment for the medical device prior to use; being lightweight; being easy (and quick) to open; and may need to allow for a user to interact with the housed device prior to opening the packaging. However, such products are typically designed with use in a medical environment (e.g. hospitals, care homes, etc.) in mind, and for this reason, little to no consideration has been given in terms of personal user experience where the packaged medical device is to be used outside of a medical environment, for example, by the patient themselves for self-catheterisation, e.g. in a public toilet.

For instance, packaging designed to be opened quickly and efficiently may take the form of a pair of sheets of material sealed about their edges to define an interior region housing the product. The sheets may be pulled apart to access the medical device housed therein. Here, each of the sheets and the housed medical device generally must be disposed of separately as the sheets serve no further purpose once the packaging is opened. It would therefore be advantageous to provide packaging wherein the number of separable components of the packaging is reduced and/or wherein the packaging may be used to hold used medical devices for subsequent disposal.

The shape and form of prior art packaging may generally be dictated in the main by the shape and form of the housed medical device itself. Where there are no or few space constraints this may not be problematic, and may actually be beneficial as the device can be housed without needing to be altered in any way—i.e. it can be housed ready for use. However, certain devices (e.g. a male urinary catheter which may be upwards of 30 cm long) may make the size and form of such packaging impractical in terms of a user carrying said packaging for personal use. Whilst the flexibility of some catheters may mean they can be housed in a coiled/folded configuration, to date no acceptable solution has been provided where this is the case. It would therefore be advantageous to provide packaging which is suitably configured to be carried by a user (e.g. in their hand, pocket or bag).

Furthermore, where packaging has been designed for a medical environment, the discreetness with which it may be used is generally not a consideration. With this in mind, there is no consideration of the noise generated upon opening such packaging. Likewise, there is generally no consideration for the number of separable components of the packaging as, in a medical environment, it is likely to be possible to dispose of such components at the point of use rather than in a separate location (which may be the case for a personal user outside of such an environment). For certain medical devices which may be used outside of a medical environment (e.g. an intermittent urinary catheter) such characteristics may be undesirable for the user. It would therefore be advantageous to provide packaging for a medical device (e.g. an intermittent urinary catheter) which allows for the carrying, use and subsequent disposal of the packaging and housed device to be performed discreetly by a user.

It is an aim of an embodiment or embodiments of the invention to overcome or at least partially mitigate one or more problems with the prior art.

SUMMARY OF THE INVENTION

According to an aspect of the invention there is provided packaging for housing a medical device.

The packaging may comprise first and second sides sealed or otherwise secured around the periphery thereof to define a plurality of edges. The plurality of edges may include one or more of a first major edge, a second major edge, a lower edge and an upper edge. The first edge may comprise a first, straight edge. The second edge may comprise a second, tapered edge which may optionally oppose the first edge.

The packaging may comprise an interaction region defining a first point of contact for a user of the packaging. The interaction region may comprise one or more visual and/or tactile indicators on the first and/or second sides of the packaging. The interaction region may be positioned proximal to the first or second edge of the packaging.

The packaging may comprise a tear-away region, which may comprise a tear line defining a line along which the packaging may be torn to at least partially separate the tear-away region from the remainder of the packaging to form an open upper end of the packaging, in use. The tear-away region may be defined proximal to the upper edge of the packaging. The tear-away region may comprise an interaction point defining a second point of contact for a user of the packaging. The interaction point may be provided at a first end of the tear-away region. The tear-away region may comprise a tear stop. The tear stop may be provided at a second end of the tear-away region. The tear stop may act to prevent or reduce the likelihood of the tear-away region being completely separated from the remainder of the packaging The tear-away region may be substantially triangular in shape having a sloped upper edge.

The packaging may comprise a sealing arrangement comprising first and second sealing members operable to provide a user-sealable seal between the first and second sides of the packaging. The first and/or second sealing members may be provided on an interior surface of the first and/or second sides of the packaging. For example, the sealing arrangement may comprise comprising a first sealing member provided on the interior surface of the first side of the packaging and a second sealing member provided on the interior surface of the second side of the packaging. The sealing arrangement may be provided proximal to the tear-away region.

At least a portion of the first and/or second sides of the packaging may comprise a material having a textured surface profile on an interior and/or exterior surface thereof.

According to an aspect of the invention there is provided packaging housing a medical device, the packaging comprising: first and second sides sealed or otherwise secured around the periphery thereof to define a pair of major edges, a lower edge and an upper edge; wherein the pair of major edges comprise: a first, straight edge; and a second, tapered edge opposing the first; an interaction region defining a first point of contact for a user of the packaging, the interaction region comprising one or more visual and/or tactile indicators on the first and/or second sides of the packaging and being positioned proximal to the first or second edge; a tear-away region defined proximal to the upper edge, the tear away region comprising: a tear line between a first end and a second end of the tear-away region defining a line along which the packaging may be torn to at least partially separate the tear-away region from the remainder of the packaging to form an open upper end of the packaging, in use; an interaction point at a first end of the tear-away region defining a second point of contact for a user of the packaging; and a tear stop at the second end of the tear-away region, the tear stop acting to prevent or reduce the likelihood of the tear-away region being completely separated from the remainder of the packaging; wherein the tear-away region is substantially triangular in shape having a sloped upper edge; and a sealing arrangement comprising a first sealing member provided on the interior surface of the first side of the packaging and a second sealing member provided on the interior surface of the second side of the packaging, the first and second sealing members being operable to provide a user-sealable seal between the first and second sides of the packaging, proximal to the tear-away region; and wherein at least a portion of the first and/or second sides of the packaging comprise a material having a textured surface profile on an interior and/or exterior surface thereof.

Advantageously, having a tapered edge opposing the straight edge of the packaging may lead a user to hold the packaging in a particular (e.g. a "user-friendly") orientation. For instance, the first, straight edge may define a leading edge of the packaging for a user when interacting with the packaging, e.g. to open the packaging. Furthermore, having tapered edge opposing the straight edge of the packaging may advantageously define the shape of the packaging to suit a user's palm and/or may be pocket shaped. Furthermore, providing a sealing arrangement in combination with a tear-away region allows for the packaging to be initially opened through at least partial removal of the tear-away portion before being sealed using the first and second sealing members. Having the sealing members provided on an interior surface of the sides of the packaging advantageously reduces the number of individual components provided as part of the packaging thereby improving the user experience, for example when compared with packaging which include an additional sealing tab. This is particularly beneficial where the packaging houses a single use medical device, for example a urinary catheter, where the packaging may subsequently be used to house a used product for disposal where reduction of the number of components and packaging parts which may need to be housed within packaging post use is desirable. The textured surface profile may act to dampen or otherwise mitigate propagation of sound waves through the packaging. As an end result, the overall sound produced upon user interaction with the packaging (e.g. opening the packaging) or indeed simply when carrying the packaging may be reduced. This may be particularly advantageous where it is desirable for the packaged medical product to be used and carried discreetly (e.g. carried in a trouser/coat pocket in a public environment, then used in a public toilet, such as in a restaurant or shopping centre).

Optional features set out below may apply to any aspect of the invention (as defined above, or below, as appropriate).

The medical device may comprise a catheter. The medical device may comprise a urinary catheter. The medical device may comprise a female urinary catheter, but is preferably a male urinary catheter. The medical device may comprise a single-use medical device. The medical device may comprise an intermittent urinary catheter.

According to an aspect of the invention there is provided packaging for housing a medical device, the packaging comprising: first and second sides sealed or otherwise secured around the periphery thereof to define a plurality of edges; wherein the plurality of edges comprise a first, straight edge and a second, tapered edge opposing the first; and an interaction region defining a point of contact for a user of the packaging, the interaction region comprising one or more visual and/or tactile indicators on the first and/or second sides of the packaging.

According to an aspect of the invention there is provided packaging housing a medical device, the packaging comprising: first and second sides sealed or otherwise secured around the periphery thereof to define a pair of major edges, a lower edge and an upper edge; wherein the pair of major edges comprise a first, straight edge and a second, tapered edge opposing the first; and an interaction region defining a point of contact for a user of the packaging, the interaction region comprising one or more visual and/or tactile indicators on the first and/or second sides of the packaging and being positioned proximal to at least the first or second major edge of the packaging.

Advantageously, having a tapered edge opposing the straight edge of the packaging may lead a user to hold the packaging in a particular (e.g. a "user-friendly") orientation. For instance, the first, straight edge may define a leading edge of the packaging for a user when interacting with the packaging, e.g. to open the packaging. Furthermore, having tapered edge opposing the straight edge of the packaging may advantageously define the shape of the packaging to suit a user's palm and/or may be pocket shaped.

The interaction region may preferably be positioned proximal to the first major edge of the packaging. Advantageously, having the interaction region provided proximal to the straight, first major edge defines a distinct region on the packaging for the user to grip, leading the user to grip the packaging at or proximal to the "leading edge" of the packaging.

In embodiments, the second major edge comprises a curved, tapered edge. Advantageously, having the second major edge both curved and tapered more clearly defines the difference between the first and second major edges, leading user interaction. Furthermore, a curved, tapered edge better complements the size/shape profile of a user's hand and/or pocket leading to increased usability of the packaging.

The lower edge of the packaging may comprise a straight edge. The straight, lower edge may be provided substantially perpendicular to the first major edge.

The upper edge of the packaging may be provided at an angle, e.g. not perpendicular, to the first and/or second major edges. In such embodiments, the upper edge may comprise a sloped edge. The sloped upper edge may slope from the first major edge to the second major edge, or from the second major edge to the first major edge, for example. The sloped upper edge may define a substantially triangular region proximal to the upper edge of the packaging.

In embodiments, the packaging comprises a tear-away region. The tear-away region may be defined proximal to the upper edge of the packaging. The tear-away region may be defined at least in part by one or more of: the upper edge of the packaging; at least a portion of the first major edge; at least a portion of the second major edge; and a tear line.

The tear line may be provided between a first end and a second end of the tear-away region. The tear line may define a line along which the packaging may be torn to at least partially separate the tear-away region from the remainder of the packaging. Tearing the packaging along the tear line may form an open upper end of the packaging, in use. In embodiments wherein the upper edge comprises a sloped upper edge, the upper edge; first major edge, or at least a portion thereof; the second major edge, or at least a portion thereof; and/or the tear line may define a substantially triangular tear-away region.

The one or more visual and/or tactile indicators may visibly indicate the position of the interaction region. The one or more visual and/or tactile indicators may be visibly distinct from the remainder of the first and/or second sides of the packaging.

The one or more visual and/or tactile indicators may comprise one or more visual surface markings. The one or more visual surface markings may comprise a pattern. The one or more visual surface markings may distinguish the interaction region from the remainder of the first and/or second side of the packaging—e.g. the one or more visual surface markings may be visually distinct from any surface markings provided on the remainder of the first and/or second side of the packaging. In preferred embodiments, the one or more visual surface markings of the interaction region may comprise a pattern and the remainder of the first and/or second side of the packaging may comprise no surface markings.

The one or more visual and/or tactile indicators may comprise a visual boundary marking. For example, the one or more visual and/or tactile indicators may comprise a solid or broken line defining a boundary of the interaction region. The visual boundary marking may comprise one or more lines which comprise substantially the same form as one or more edges of the packaging. For instance, the visual boundary marking may comprise a first, tapered line which comprises substantially the same curvature and/or tapering as the second major edge of the packaging. The visual boundary marking may comprise a second, straight line substantially parallel to the lower edge of the packaging. The first and second lines of the visual boundary marking may meet at a radiused corner.

The tactile indicator(s) may be provided on an exterior surface of the first and/or second sides of the packaging. The one or more visual and/or tactile indicators may comprise a tactile surface profile on the exterior surface of the first and/or second sides of the packaging. For example, the one or more visual and/or tactile indicators may comprise a raised, lowered or patterned surface profile such as a tactile surface texture. The tactile surface profile may assist with a user gripping the packaging at the interaction region.

In embodiments, the packaging has a height of at least 50 mm, or at least 75 mm, or at least 100 mm, or at least 125 mm, or at least 150 mm, or at least 200 mm, for example. The packaging may have a height of no more than 100 mm, or no more than 125 mm, or no more than 150 mm, or no more than 200 mm, or no more than 250 mm, for example. In embodiments, the packaging has a width of up to 50 mm, or up to 75 mm, or up to 100 mm, or 125 mm, or up to 150 mm, for example. In some embodiments the packaging has a width of at least 50 mm, or at least 75 mm, or at least 100 mm, or at least 120 mm, or at least 150 mm, for example. The packaging may have a width of no more than 100 mm, or no more than 120 mm, or no more than 150 mm, or no more than 200 mm, for example. In some embodiments the packaging has outer dimensions of no more than 180 mm in height and no more than 120 mm in width.

In some embodiments the first and second sides are sealed around the periphery thereof via one or more of a heat seal, pressure seal, or weld, for example.

At least two of the first major edge, second major edge, lower edge, and upper edge may be integrally formed at ends thereof with a further edge of the packaging at radiused corners. In some embodiments, each of the edges are integrally formed at ends thereof with a further edge of the packaging at radiused corners. In embodiments wherein there is provided a plurality of radiused corners, each radiused corner may comprise a corner radius equal to the remaining radiused corners of the packaging. In some embodiments a first radiused corner of the packaging may comprise a larger corner radius compared with one or more further radiused corners of the packaging. The first radiused corner may be provided between the first major edge and the upper edge. The first radiused corner may be provided within the interaction region. The first radiused corner may be provided as part of the tear-away region.

According to an aspect of the invention there is provided packaging housing a medical device, the packaging comprising: first and second sides sealed or otherwise secured around the periphery thereof; a tear-away region defined proximal to an upper edge of the packaging which may be at least partially removed from the remainder of the packaging to form an open upper end of the packaging, in use; and a sealing arrangement comprising first and second sealing members operable to provide a user-sealable seal between the first and second sides of the packaging at or proximal to the open upper end of the packaging.

According to another aspect the invention there is provided packaging housing a medical device, the packaging comprising: first and second sides sealed or otherwise secured around the periphery thereof; a tear-away region defined proximal to an upper edge of the packaging, the tear away region comprising a tear line between a first end and a second end of the tear-away region defining a line along which the packaging may be torn to at least partially separate the tear-away portion from the remainder of the packaging to form an open upper end of the packaging, in use; and a sealing arrangement comprising a first sealing member provided on the interior surface of the first side of the packaging and a second sealing member provided on the interior surface of the second side of the packaging, the first and second sealing members being operable to provide a user-sealable seal between the first and second sides of the packaging at or proximal to the open upper end of the packaging.

Advantageously, providing a sealing arrangement in combination with a tear-away region allows for the packaging to be initially opened through at least partial removal of the tear-away portion before being sealed using the first and second sealing members. Having the sealing members provided on an interior surface of the sides of the packaging advantageously reduces the number of individual components provided as part of the packaging thereby improving the user experience, for example when compared with packaging which include an additional sealing tab. This is particularly beneficial where the packaging houses a single use medical device, for example a urinary catheter, where the packaging may subsequently be used to house a used product for disposal where reduction of the number of components and packaging parts which may need to be housed within packaging post use is desirable.

The user-sealable seal may comprise a resealable seal.

The first and second sealing members may be configured to provide an adhesive seal between the first and second sides of the packaging. In such embodiments, one or both of the first and second members may comprise an adhesive material applied to a surface of the first and/or second side of the packaging. For example, in some embodiments the first sealing member may comprise an adhesive material applied to an interior surface of the first side of the packaging. In such embodiments, the second sealing member may comprise an adhesive material applied to an interior surface of the second side of the packaging. Alternatively, only the first sealing member may comprise an adhesive material. In such embodiments, the second sealing member may comprise a region of one of the sides of the packaging configured to be adhesively secured to the adhesive material of the first sealing member.

In some embodiments the first and second sealing members may form a hook and loop fastener arrangement. In such embodiments, the first sealing member may comprise a region of hook fasteners located on a surface of the first side of the packaging, and the second sealing member may comprise a region of loop fasteners located on a surface of the second side of the packaging. In alternative embodiments, the first and second sealing members may form a double hook fastener arrangement. In such embodiments, the first sealing member may comprise a region of hook fasteners located on a surface of the first side of the packaging, and the second sealing member may comprise a region of hook fasteners located on a surface of the second side of the packaging.

The first and second sealing members may provide a water resistant, or a near or substantially water-tight seal at or proximal to the open upper end of the packaging. Advantageously, such an arrangement may be useful in instances where fluid may be present within the packaging before or after use, for example where the packaged product is a urinary catheter and the packaging includes a fluid therein such as a lubricant or wetting fluid, or when traces of urine may be present in/on a used catheter which is re-introduced to the packaging for disposal.

In embodiments, the tear-away region comprises an interaction point. The interaction point may be provided at a first end of the tear-away region. The interaction point may define a point of contact for a user of the packaging.

In embodiments, the interaction point comprises an aperture in the packaging. The aperture may, for example, comprise a circular aperture in the packaging. The aperture may be provided through the first and/or second sides of the packaging. In embodiments, interaction point comprises a radiused corner of the packaging. The radiused corner may comprise a first radiused corner of a plurality of radiused corners of the packaging. The first radiused corner of the packaging may comprise a larger corner radius compared with one or more further radiused corners of the packaging. The first radiused corner may be provided between the first major edge and the upper edge, for example.

The tear-away region may comprise a tear stop. The tear stop may be provided at a second end of the tear-away region. The second end of the tear-away region may comprise an opposing end of the tear-away region to the first end. In this way, the user may interact with an interaction point at the first end of the tear-away region to tear the packaging from the first end towards the second end of the tear-away region. The tear stop may act to reduce the likelihood of the tear-away region being completely separated from the remainder of the packaging. Advantageously, preventing the tear-away region from being completely separated from the remainder of the packaging reduces the number of separate components of the packaging post use. This may be beneficial from a user interaction point of view where it would be desirable to have the used medical device and any packaging components contained within, or at least be integrally formed or otherwise attached to, a single package for subsequent disposal.

In embodiments, the tear stop comprises an aperture within the tear-away region. The aperture may be provided on or proximal to the tear line such that, in use, a tear may propagate through the packaging towards the tear stop.

In some embodiments the tear-away region comprises a tear start. The tear start may be provided at the first end of the tear-away region. The tear start may act to initiate tearing along the tear line, e.g. from the tear start to the tear stop. The tear start may comprise a notch in first and/or second sides of the packaging. The tear start may be substantially triangular in shape. in such embodiments, the triangular notch may comprise a sloped upper edge. Optionally, the triangular notch may comprise a lower edge which may be aligned with the tear line and/or perpendicular to a first major edge of the packaging, for example.

The tear line may comprise a line of weakness in the first and/or second sides of the packaging. Advantageously, providing a tear line as a line of weakness may encourage a tear to propagate in a desired direction, e.g. from a first end of the tear-away region to a second end of the tear-away region.

The tear-away region of the packaging may be defined at least in part by first and second major edges of the packaging, and upper edge of the packaging, and the tear line. The upper edge of the packaging may be provided at an angle, e.g. not perpendicular, to the first and/or second major edges. In such embodiments, the upper edge, and hence the tear-away region, may comprise a sloped upper edge. In this way, the tear-away region may be substantially triangular in shape.

In some embodiments the sloped upper edge may slope from the interaction point to the tear stop. Advantageously, such an arrangement may encourage the user interact with the interaction point to open the packaging.

In embodiments, the packaging may be gas impermeable and may be sealed or otherwise secured around the periphery of the first and second sides of the packaging so as to provide a sterile internal environment.

According to another aspect of the invention there is provided packaging housing a medical device, the packaging comprising first and second sides sealed or otherwise secured around the periphery thereof; wherein at least a portion of the first and/or second sides of the packaging comprise a material having a textured surface profile on a surface thereof.

Advantageously, the textured surface profile may act to dampen or otherwise mitigate propagation of sound waves through the packaging. As an end result, the overall sound produced upon user interaction with the packaging (e.g. opening the packaging) may be reduced. This may be particularly advantageous where it is desirable for the packaged medical product to be used discreetly (e.g. in public).

The textured surface profile may be provided on an exterior surface of the first and/or second sides of the packaging. Additionally or alternatively, the textured surface profile may be provided on an interior surface of the first and/or second sides of the packaging. Advantageously, having the textured surface profile provided on the interior surface of the first and/or second sides of the packaging may provide the above-mentioned advantages without substantially affecting the design of the exterior surface(s) of the packaging.

The textured surface profile may comprise a patterned surface profile. In some embodiments the textured surface profile may comprise an undulating surface profile. In further embodiments the textured surface profile may comprise an irregular or random surface profile. The packaging may be embossed or lacquered to form the textured surface profile.

The packaging may be formed, at least in part, from one or more of: polypropylene (PP), polyethylene (PET) or orientated polypropylene (OPP), for example. The packaging may comprise a laminate of two or more layers. The packaging may comprise an inner layer and an outer layer. The packaging may comprise inner and outer layers of polypropylene. The packaging may comprise an inner layer of orientated polypropylene and an outer layer of polypropylene. The packaging may comprise an inner layer of polypropylene and an outer layer of polyethylene, for example. The inner layer and outer layer may have the same thickness. In other embodiments, the inner layer and outer layer may have different thicknesses. The inner layer may have a smaller thickness than the outer layer. In embodiments, the inner layer may have a thickness of between 5-20 microns, or between 10-10 microns, or between 10-15 microns, and the outer layer may have a thickness of between 10-50 microns, or between 20-40 microns, or between 35-45 microns. In one example, the inner layer may have a thickness of approximately 12 microns and the outer layer may have a thickness of approximately 40 microns.

According to an aspect of the invention there is provided a packaging blank for forming the packaging of any aspect described herein.

The packaging blank may comprise first and second side panels. The first and/or second side panels may comprise any one or more of: a first edge, a second edge, a lower edge; and an upper edge. The first edge(s) of the first and/or second side panel may comprise a straight edge. The second edge(s) of the first and/or second side panel may comprise a tapered edge. The tapered second edge(s) may comprise a curved tapered edge. The lower edge(s) of the first and/or second side panel may comprise a straight edge. The upper edge(s) of the first and/or second side panel may comprise a sloped edge.

The first and second side panels may be configured to be sealed about their periphery to the other side panel to form the packaging. The panels may be configured to be sealed to the other side panel at or proximal to the first edge, second edge, lower edge and/or upper edge. The panels may be configured such that the upper edge, lower edge, first edge and second edge of the first panel is configured to be sealed to corresponding upper, lower, first and second edges on the second panel.

The first and second side panels of the packaging blank may be provided as separate components. Alternatively, the first and second side panels may be provided integrally formed with one another. For example, the first and second side panels may be integrally formed along an edge thereof, e.g. respective first edges of the first and second side panels. The first and second side panels may be integrally formed at a fold line about which the packaging blank may be folded to at least partially form the packaging.

The first and/or second side panels may comprise one or more apertures therein. The aperture(s) may be provided to form an interaction point in the formed packaging—e.g. an aperture within a tear-away region of the packaging. The aperture(s) may be provided to form a tear-stop in the formed packaging—e.g. an aperture on a tear line. The aperture(s) may be provided to form a tear-start in the formed packaging—e.g. to form a notch within an edge of the formed packaging.

The first and/or second side panels may include a sealing member formed, coupled, sealed or otherwise secured thereto. For example, the first and/or second side panels may comprise a sealing member adhesively secured to the surface of the panel. In some embodiments, the first side panel comprises a first sealing member and the second side panel comprises a second sealing member. The sealing member(s) may comprise a strip of material, such as a strip of adhesive material, a strip of hook fasteners or a strip of loop fasteners, for example.

According to an aspect of the invention there is provided a packaging blank for forming the packaging of any preceding claim, the packaging blank comprising first and second side panels configured to be sealed about their periphery to the other side panel to form the packaging.

The packaging blank of this aspect of the invention may comprise any one or more of the optional features discussed in relation to the preceding aspect as desired or appropriate.

According to an aspect of the invention there is provided a method of manufacturing packaging of any aspect described herein, the method comprising sealing or otherwise securing first and second sides of the packaging about a periphery thereof to define an internal volume housing the medical device.

The method may comprise forming the packaging about the medical device. In such embodiments, the medical device may be placed on or otherwise associated with one of the first or second sides of the packaging, before the first and second sides are sealed about the periphery to enclose the medical device.

In other embodiments the method may comprise partially forming the packaging, introducing the medical device into the part formed packaging, and subsequently forming the remainder of the packaging about the medical device. For example, in some embodiments the method may comprise partially sealing or otherwise securing the first and second sides of the packaging about their periphery to partially form a packaging with an open end for introduction of the medical device. In such embodiments, the method may comprise introducing the medical device into the packaging through the open end, before subsequently sealing or otherwise securing the remainder of the periphery of the first and second sides to enclose the medical device.

The method may comprise forming the packaging from a packaging blank according to any aspect described herein.

DETAILED DESCRIPTION OF THE INVENTION

In order that the invention may be more clearly understood one or more embodiments thereof will now be described, by way of example only, with reference to the accompanying drawings, of which.

In general, the invention relates to packaging 10 housing a medical device, shown herein as a medical device in the form of a male intermittent, single use urinary catheter 100.

FIGS. 1A-4 illustrate an embodiment of packaging 10, which in this embodiment is formed of polypropylene. The packaging 10 includes a first side 12 and a second side 14 sealed about their periphery. Here, the first and second sides 12, 14 are heat sealed about their periphery to form an enclosed packaging 10 for the catheter 100. Sealing of the first and second sides 12, 14 about their peripheries acts to define a pair of opposing major edges 16, 18, and opposing lower and upper edges 20, 22 of the packaging 10.

Figure 1A:
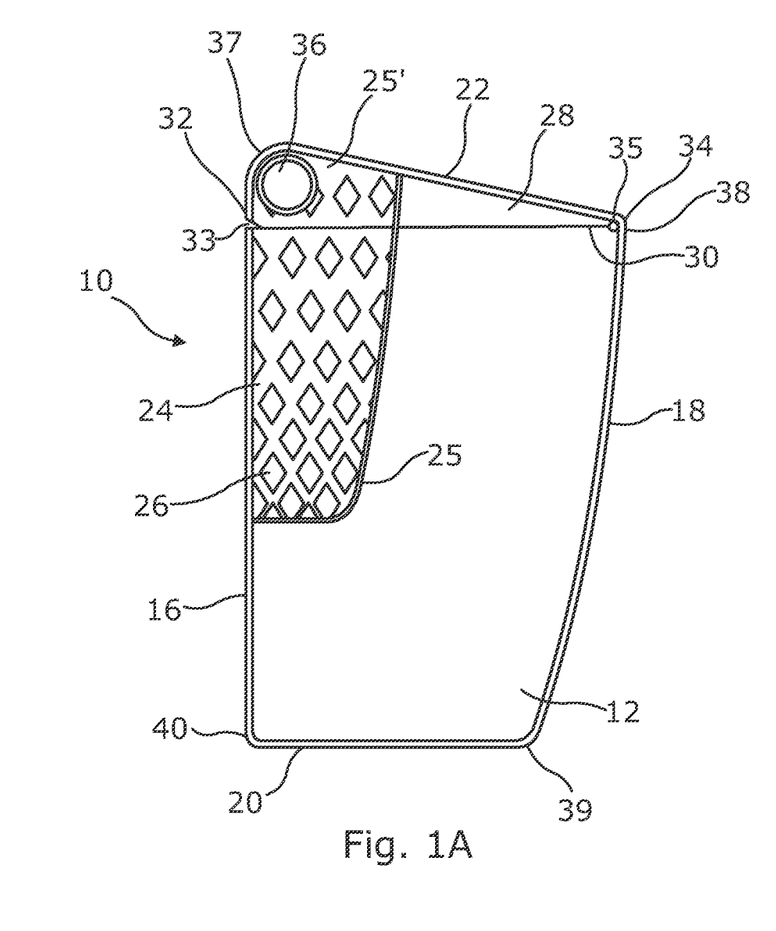
FIG. 1A is a front view of an embodiment of packaging according to the invention.
Figure 1B:
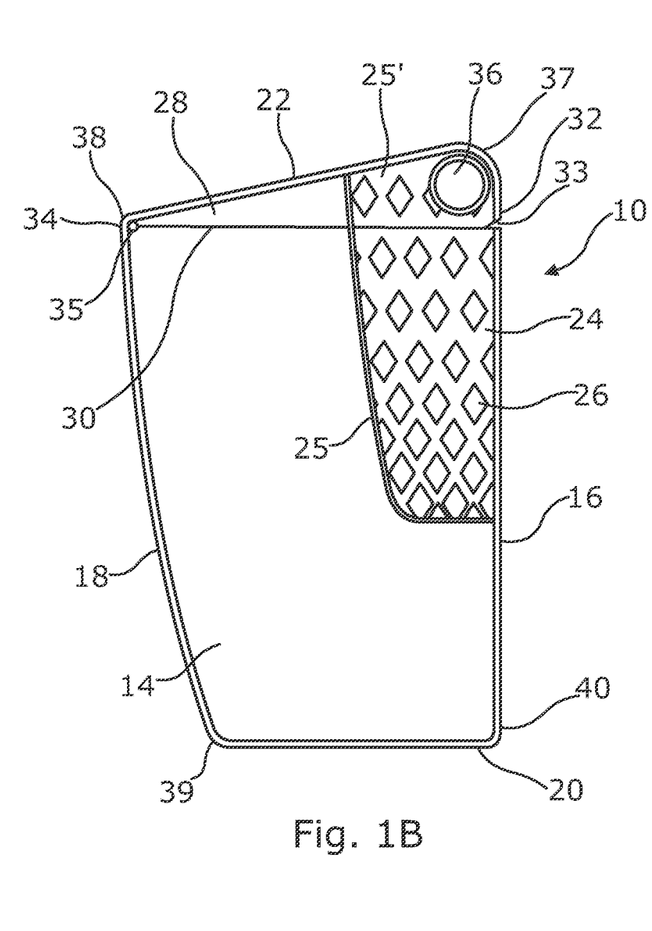
FIG. 1B is a rear view of the packaging shown in FIG. 1A.
Figure 2:
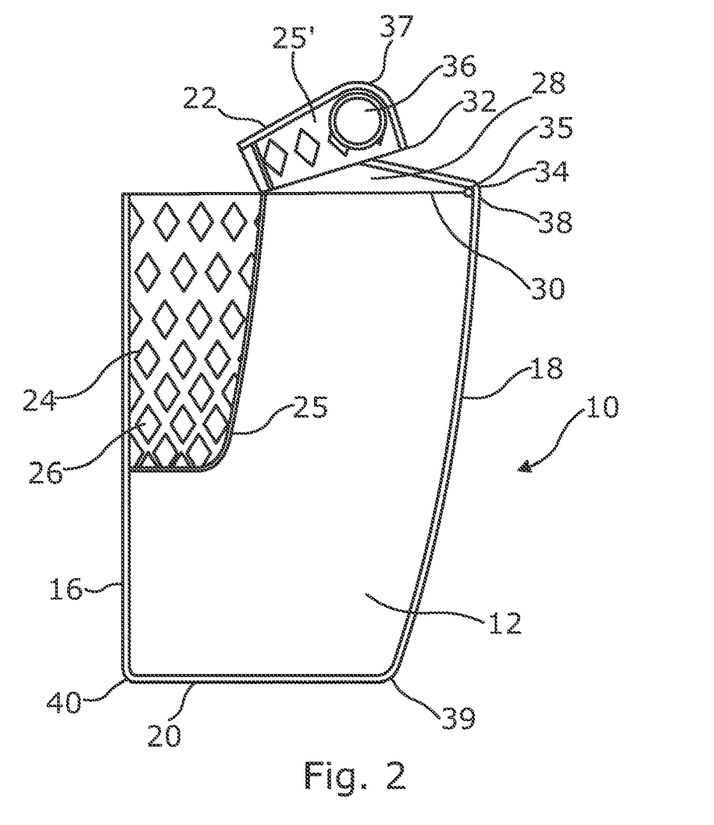
FIG. 2 is a further front view of the packaging shown in the preceding Figures with the packaging partially opened.

The first major edge 16 is substantially straight and defines a leading edge of the packaging 10, in use. The second major edge 18 is tapered and curves from the upper edge 22 to the lower edge 20. The lower edge 20 is also straight, whilst the upper edge 22 is straight but slopes (downwards in the orientation shown in the Figures) from the first major edge 16 to the second major edge 18. As described herein, the sloped upper edge 22 partially defines a tear-away region 28 of the packaging 10.

The edges 16, 18, 20, 22 meet respective adjacent edges 16, 18, 20, 22 at ends thereof at radiused corners. Specifically, the first major edge 18 and upper edge 22 meet at a first radiused corner 37, the upper edge 22 and second major edge 18 meet at a second radiused corner 38, the second major edge 18 and the lower edge 20 meet at a third radiused corner 39 and the lower edge 20 and the first major edge 16 meet at a fourth radiused corner 40. The second, third and fourth radiused corners 38, 39, 40 each comprise equal corner radiuses. In contrast, the first radiused corner 37 comprises a larger corner radius. As discussed herein, the first radiused corner 37 is provided as part the tear-away region 28 and is provided to define part of a secondary interaction point on the packaging 10.

An interaction region 24 is provided which defines a primary interaction point (e.g. a first point of contact) for a user of the packaging 10. The interaction region 24 is located proximal to the first major edge 16 of the packaging 10 and extends from midway along the first edge 16 to the upper edge 22. The interaction region 24 includes visual indicators in the form of surface markings 26. The surface markings 26 are provided on both the first and second sides 12, 14 of the packaging 10 and, in this embodiment, take the form of a series of diamonds. It will be appreciated that the invention is not limited in this sense, but rather the interaction region 24 need only be distinguished in some manner from the remainder of the packaging 10. This can take the form of different surface patterns, textures, colours etc. between the interaction region 24 and the remainder of the packaging, or may simply be defined by a boundary line (see below).

In the illustrated embodiment, the interaction region 24 is bounded by a boundary line 25. The boundary line 25 takes substantially the same form as the second major edge 18 and the lower edge 20 of the packaging 10. Specifically, the boundary line 25 includes a first, tapered line which comprises substantially the same curvature and tapering as the second major edge 18 of the packaging 10, and a second, straight line substantially parallel to the lower edge 20 of the packaging 10. The first and second lines of the boundary line 25 meet at a radiused corner.

The interaction region 24, in effect, defines a gripping region for the packaging 10 leading a user to grip the packaging 10 at the first (i.e. the "leading") edge 16 of the packaging 10.

Packaging 10 includes a tear-away region 28 defined proximal to the sloped upper edge 22. Specifically, in the illustrated embodiment, the packaging 10 includes a substantially triangular tear-away region 28 defined by the upper edge 22, a portion of the first major edge 16 and a tear line 30 defined between first and second ends 32, 34 of the tear-away region 28. The tear-away region 28 comprises a portion of the packaging 10 which may be at least partially removed, in use, to form an open upper end of the packaging 10, enabling access to the interior of the packaging 10.

The tear line 30 is shown as a substantially straight line between the first end 32 and the second end 34 of the tear-away region 28. At the first end 32, a notch 33 is provided in the packaging which acts as a tear start for initiating a tear along (or at least partly along or proximal to) the tear line 30. Here, the notch is triangular in shape with a sloped upper edge and a flat lower edge which is aligned with the tear line 30, which may act to control the direction of the tear through the packaging, in use, e.g. preferably along the tear line 30. At the second end 34 of the tear-away region 28, a tear stop in the form of an aperture 35 in the packaging 10 is provided. The aperture 35 acts to prevent or reduce the likelihood of the tear-away region 28 being completely removed from the remainder of the packaging 10. Specifically, the aperture prevents further propagation (or at least reduces the likelihood of further propagation) of a tear along (or substantially along) the tear line 30. In this way, the tear-away region 28 is configured to remain integrally formed at the second end 34 to the remainder of the packaging 10 after opening. Advantageously, the packaging 10 is retained as a single piece packaging, even after opening, thereby increasing ease of use by the user (e.g. in terms of subsequent disposal).

As discussed herein, a secondary interaction point (e.g. a second point of contact for the user) is provided within the tear-away region 28. Specifically, this takes the form of an aperture 36 provided through the packaging 10 positioned proximal to the first radiused corner 37. The aperture 36 is sized to roughly correspond to the typical size of a finger/thumb tip, so as to be gripped by a user's finger and thumb, in use. It may also conveniently act as a hanger. In addition, the interaction region 24 extends upwards into the tear-away region 28 defining a secondary interaction region 25' within the tear-away region 28 provided about the aperture 36. This further acts to lead a user to grip the packaging 10 at the secondary interaction region 25' (i.e. at or proximal to the aperture 36) when opening the packaging 10.

In use, the user may first grip the packaging 10 at the interaction region 24 with a first hand, before gripping the tear-away region 28 at or proximal to the aperture 36 with a second hand. The tear-away region 28 and the remainder of the packaging 10 may then be pulled in opposing directions to cause tearing along the tear line 30, beginning at the notch 33 at the first end 32 of the tear-away region 28 towards the aperture 35 at the second end 34 of the tear-away region 28. This is shown figuratively in FIG. 2.

Figure 3:
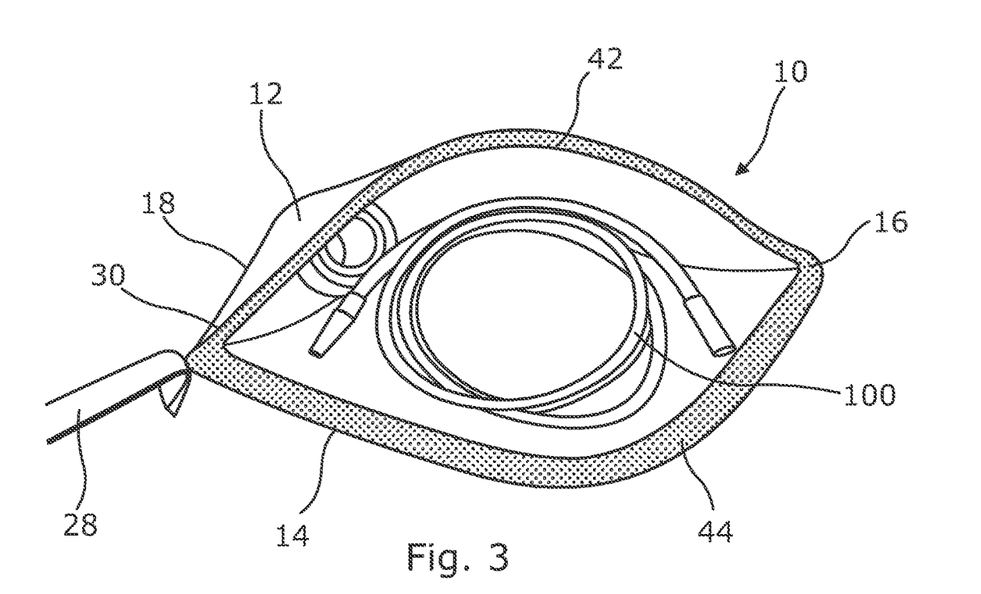
FIG. 3 is a plan view of the (opened) packaging shown in the preceding Figures.
Figure 4:
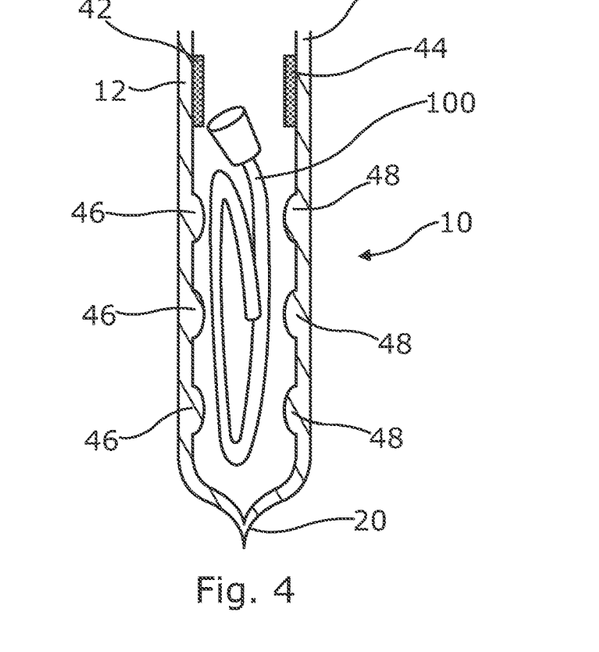
FIG. 4 is a side cross sectional view of the (opened) packaging shown in the preceding Figures.

The packaging 10 additionally includes a sealing arrangement which takes the form of a first sealing member 42 provided on the interior surface of the first side 12 of the packaging 10 and a second sealing member 44 provided on the interior surface of the second side 14 of the packaging 10. The first and second sealing members 12, 14 are operable to provide a user-sealable seal between the first and second sides 12, 14, specifically at an open upper end of the packaging 10 formed through removal of the tear-away region 28. In the illustrated embodiment, each of the first and second sealing members 42, 44 take the form of a strip of hook fasteners which is secured (e.g. adhesively) to the interior surface of the respective side 12, 14 of the packaging 10. In this way, the first and second sealing members 42, 44 form a double hook fastener arrangement for sealing the open upper end of the packaging 10, in use. In this way, the medical device (e.g. catheter 100) can be removed from the packaging 10, used, and then returned to the packaging 10 for subsequent disposal. Configuring the packaging 10 such that it is sealable following opening may be beneficial in situations wherein liquid might be present (e.g. urine or wetting fluid for catheter 100), and/or where a user wishes to keep the contents of the packaging 10 discreet, e.g. on exit from a toilet cubicle before disposal.

As shown in FIG. 4, each of the first and second sides 12, 14 of the packaging includes a textured surface profile provided on its interior surface. Specifically, each of the first and second sides 12, 14 comprises an undulating surface profile formed of a series of regions 46, 48 of increased thickness provided in respective sides 12, 14. Advantageously, the textured surface profile acts to dampen or otherwise mitigate propagation of sound waves through the packaging 10. As an end result, the overall sound produced upon user interaction with the packaging 10 (e.g. rustling in a pocket, or on opening the packaging 10) can be reduced when compared with prior art packaging.

In the illustrated embodiment the packaging 10 includes an interaction region 24 which includes a series of visual indicators 26. Additionally or alternatively, the interaction region 24 may incorporate one or more tactile indicators within the interaction region 24. For example, the tactile indicators may comprise one or more areas within the interaction region 24 having a raised (or lowered) surface to provide a textured surface profile. Advantageously, this may physically distinguish the interaction region 24 from the remainder of the packaging 10, and may also assist with a user gripping the packaging 10, in use.

In the illustrated embodiment the packaging 10 is provided with first and second sealing members 42, 44 in the form of strips of hook fasteners adhesively secured to the inner surface of the first and second sides 12, 14. However, it will be appreciated that the sealing members 42, 44 may alternatively form a hook and loop fastener arrangement with, for example, the first sealing member 42 comprises a strip of hook fasteners adhesively secured to the first side 12, and the second sealing member 44 taking the form of a strip of loop fasteners adhesively secured to the second side 14 of the packaging 10, or vice versa. Alternatively, the first and second sealing members 42, 44 may comprise an adhesive material for providing an adhesive seal between the first and second sides 12, 14 of the packaging 10.

Figure 5:
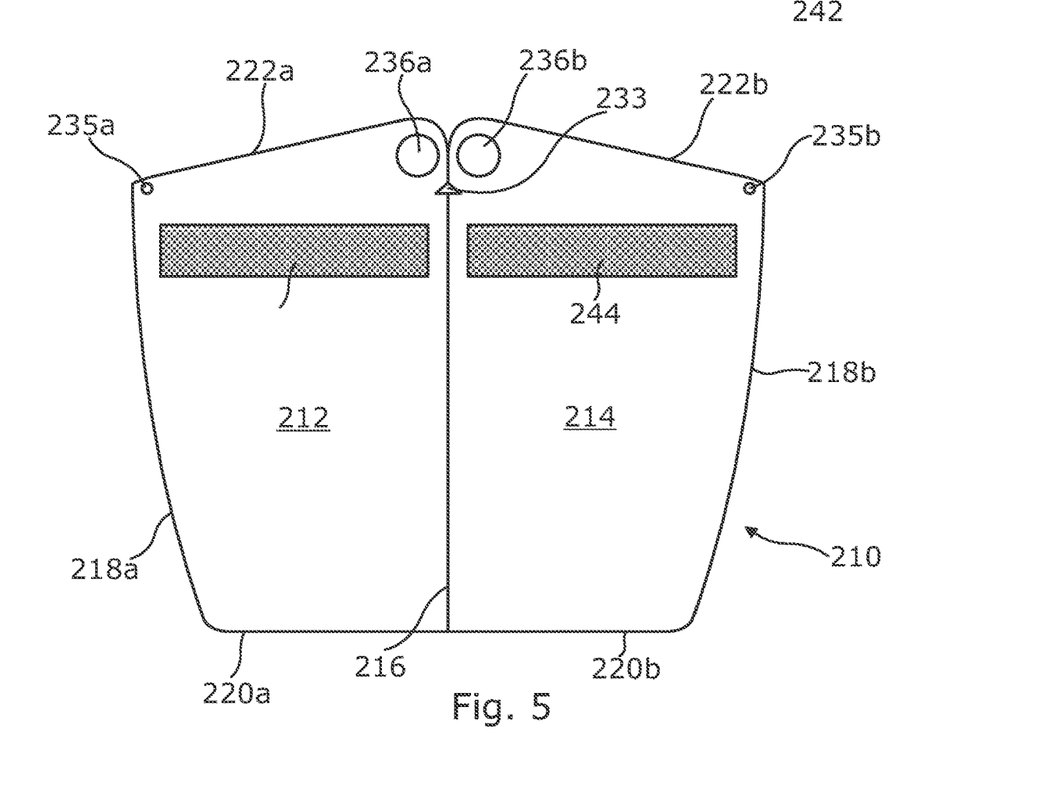
FIG. 5 illustrates an embodiment of a packaging blank in accordance with the invention.

FIG. 5 illustrates an embodiment of a packaging blank 210 for forming packaging 10.

The blank 210 comprises a first side panel 212 and a second side panel 214 for forming first and second sides 12, 14 of the packaging 10, respectively. In the illustrated embodiment, the first and second side panels 212, 214 are integrally formed along a first edge thereof at fold line 216.

The first side panel 212 comprises a second edge 218a, lower edge 220a and upper edge 222a, which together with the fold line 216 define the periphery of the first side panel 212. The first side panel 212 additionally includes a first aperture 235a and second aperture 236a provided through the panel 212. A strip of hook fasteners 242 is provided on the surface of the side panel 212 forming a first sealing member 42 of the packaging 10.

The second side panel 214 is configured in substantially the same manner as first side panel 212 and comprises a second edge 218b, lower edge 220b and upper edge 222b, which together with the fold line 216 define the periphery of the second side panel 214. The second side panel 214 additionally includes a first aperture 235b and second aperture 236b provided through the panel 214. A strip of hook fasteners 244 is provided on the surface of the side panel 214 forming a second sealing member 42 of the packaging 10.

A further aperture 233 is provided on the fold line 216, for forming the notch 33 in the packaging 10.

To form the packaging 10, the blank 210 is folded along fold line 216 bringing corresponding edges of the blank 210 proximal to one another. Specifically, second edge 218a of the first side panel 212 is brought proximal to second edge 218b of the second side panel 214, lower edge 220a of the first side panel 212 is brought proximal to the lower edge 220b of the second side panel 214, and the upper edge 222a of the first side panel 212 is brought proximal to the upper edge 222b of the second side panel 214. The first and second side panels 212, 214 are then sealed about their periphery, specifically sealing edges 218a, 220a, 222a to respective edges 218b, 220b, 22b to form packaging 10. A seal may also be provided along fold line 216 to strengthen packaging 10 at that point. In addition, first apertures 235a, 235b are sealed to one another about their peripheries to form aperture 35 in the packaging 10, and second apertures 236a, 236b are sealed to one another about their peripheries to form aperture 36 in the packaging 10.

The catheter 100 may be located on a panel 212, 214 of the blank 210 prior to forming the packaging 10. In this instance, the blank 210 may be folded and sealed about the catheter 100 to form the packaging 10 therearound. Alternatively, the catheter 100 may be located during the forming steps. For instance, the packaging 10 may be formed by initially sealing one or more, e.g. the lower edges 220a, 220b, and second edge 218a, 218b, together with the fold line 216 to partially form a packaging having an open upper end into which the catheter 100 may be located. Here, the upper edges 222a, 222b of the blank 210 may then be sealed to one another to enclose the catheter 100 within the packaging 10. Those skilled in the art will be familiar with fold-fill-seal machinery that may be suitable for or be adapted to carry out these steps.

In a variant, the packaging blank 210 instead comprises separate first and second side panels 212, 214. That is, the fold line 216 is omitted and instead each of the first and second side panels may comprise respective first edges. These first edges may be sealed to one another as per the second edges 218a, 21b, lower edges 220a, 220b and upper edges 222a, 222b to form a first major edge 16 of the packaging 10.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Except in Examples, or where otherwise explicitly indicated, all numerical quantities in this description specifying amounts of materials, device dimension, and the like, are to be understood as modified by the word "about."

Unless otherwise indicated, each chemical or composition referred to herein should be interpreted as being a commercial grade material which may contain the isomers, by-products, derivatives, and other such materials which are normally understood to be present in the commercial grade.

The one or more embodiments are described above by way of example only. Many variations are possible without departing from the scope of protection afforded by the appended claims.

The invention claimed is:

1. Packaging housing an intermittent catheter, the packaging comprising:
   first and second side walls sealed or otherwise secured around a periphery thereof to define a pair of major edges, a lower edge and an upper edge; wherein the pair of major edges comprise: a first, straight edge; and a second, tapered edge opposing the first and tapering from the upper edge to the lower edge;
   an interaction region defining a first point of contact for a user of the packaging, the interaction region comprising one or more visual and/or tactile indicators on the first and/or second side walls of the packaging and being positioned proximal to the first or second edge;
   a tear-away region defined proximal to the upper edge, the tear-away region comprising: a tear line between a first end and a second end of the tear-away region defining a line along which the packaging may be torn to at least partially separate the tear-away region from a remainder of the packaging to form an open upper end of the packaging, in use; an interaction point at a first end of the tear-away region defining a second point of contact for a user of the packaging; and a tear stop at the second end of the tear-away region, the tear stop acting to prevent or reduce the likelihood of the tear-away region being completely separated from the remainder of the packaging; wherein the tear-away region is triangular in shape formed in part by the upper edge sloping from the interaction point to the tear stop; and
   a sealing arrangement comprising a first sealing member provided on an interior surface of the first side wall of the packaging and a second sealing member provided on an interior surface of the second side wall of the packaging, the first and second sealing members being operable to provide a user-sealable seal between the first and second side walls of the packaging, proximal to the tear-away region;
   wherein at least a portion of the first and/or second side walls of the packaging comprise a material having a textured surface profile on the interior and/or an exterior surface thereof.

2. Packaging housing an intermittent catheter, the packaging comprising:
   first and second side walls sealed or otherwise secured around a periphery thereof to define a pair of major edges, a lower edge and an upper edge; wherein the pair of major edges comprise a first, straight edge and a second, tapered edge opposing the first and tapering from the upper edge to the lower edge; and
   an interaction region defining a point of contact for a user of the packaging, the interaction region comprising one or more visual and/or tactile indicators on the first and/or second side walls of the packaging and being positioned proximal to at least the first or second major edge of the packaging.

3. Packaging as claimed in claim 2, wherein the interaction region is positioned proximal to the first major edge of the packaging.

4. Packaging as claimed in claim 2, wherein the tapered edge comprises a curved edge.

5. Packaging as claimed in claim 2, wherein the upper edge of the packaging is provided at an angle to the first and/or second major edges, defining a triangular region proximal to the upper edge of the packaging.

6. Packaging as claimed in claim 2, comprising a tear-away region defined proximal to the upper edge of the packaging.

7. Packaging as claimed in claim 2, wherein the one or more visual and/or tactile indicators comprise one or more visual surface markings.

8. Packaging as claimed in claim 2, wherein the one or more visual and/or tactile indicators comprise a visual boundary marking.

9. Packaging as claimed in claim 2, wherein the one or more visual and/or tactile indicators comprise a tactile surface profile provided on an exterior surface of the first and/or second side walls of the packaging.

10. Packaging as claimed in claim 2, wherein at least two of the first major edge, second major edge, lower edge, and upper edge are integrally formed at end thereof with a further edge of the packaging at radiused corners.

11. Packaging as claimed in claim 10, wherein a first radiused corner of the packaging comprises a larger corner radius compared with one or more further radiused corners of the packaging.

12. Packaging as claimed in claim 1, wherein the textured surface profile is provided on the interior surface of the first and/or second side walls of the packaging.

13. Packaging as claimed in claim 1, wherein the textured surface profile comprises one or more of: a patterned surface profile; an undulating surface profile; and an irregular or random surface profile.

14. Packaging housing an intermittent catheter, the packaging comprising:
   first and second side walls sealed or otherwise secured around a periphery thereof;
   an upper edge, a lower edge opposite the upper edge, a straight edge extending from the upper edge to the lower edge, and a curved edge opposite the straight edge and extending and curving from the upper edge to the lower edge;
   a triangular tear-away region defined proximal to an upper edge of the packaging, the tear-away region defined at least by the upper edge, at least a portion of a first major edge, and_a tear line between a first end and a second end of the tear-away region defining a line along which the packaging may be torn to at least partially separate the tear-away region from a remainder of the packaging to form an open upper end of the packaging, in use; and
   a sealing arrangement comprising a first sealing member provided on the interior surface of the first side wall of the packaging and a second sealing member provided on the interior surface of the second side wall of the packaging, the first and second sealing members being operable to provide a user-sealable seal between the first and second side walls of the packaging at or proximal to the open upper end of the packaging.

15. Packaging as claimed in claim 14, wherein the user-sealable seal comprises a resealable seal.

16. Packaging as claimed in claim 14, wherein the first and second sealing members form a double hook fastener arrangement, with the first sealing member comprising a region of hook fasteners located on a surface of the first side wall of the packaging, and the second sealing member comprising a region of hook fasteners located on a surface of the second side wall of the packaging.

17. Packaging as claimed in claim 14 wherein the first and second sealing members are configured to provide a water resistant or near or water-tight seal at or proximal to the open upper end of the packaging.

18. Packaging as claimed in claim 14, wherein the tear-away region comprises an interaction point defining a point of contact for a user of the packaging.

19. Packaging as claimed in claim 16, wherein the interaction point comprises an aperture in the packaging.

20. Packaging as claimed in claim 16, wherein the upper edge of the packaging is provided at an angle to a first and/or second major edges, thereby defining a sloped upper edge of the tear-away region, and wherein the sloped upper edge slopes from the interaction point to a tear stop.

21. Packaging as claimed in claim 14, wherein the tear-away region comprises a tear stop.

22. Packaging as claimed in claim 18, wherein the tear stop comprises an aperture within the tear-away region.

23. Packaging as claimed in claim 14, wherein the tear-away region comprises a tear start.

24. Packaging as claimed in claim 23, wherein the tear start comprises a notch in first and/or second side walls of the packaging.

25. Packaging housing an intermittent catheter, the packaging comprising;
    first and second side walls sealed or otherwise secured around a periphery thereof
    an upper edge;
    a lower edge opposite the upper edge;
    a straight edge extending from the upper edge to the lower edge; and
    a curved edge opposite the straight edge and extending and curving from the upper edge to the lower edge;
    wherein at least a portion of the first and/or second side walls of the packaging comprise a material having a textured surface profile on a surface thereof.

26. Packaging as claimed in claim 25, wherein the textured surface profile is provided on an interior surface of the first and/or second side walls of the packaging.

27. Packaging as claimed in claim 25, wherein the textured surface profile comprises one or more of: a patterned surface profile; an undulating surface profile; and an irregular or random surface profile.

28. Packaging as claimed in claim 25, wherein the intermittent catheter comprises a male intermittent urinary catheter.

29. Packaging as claimed in claim 25, further comprising a packaging blank for forming the packaging, the packaging blank comprising first and second side panels configured to be sealed about their periphery to the other side panel to form the packaging.

* * * * *